United States Patent
Torres (10) Patent No.: US 10,821,264 B1
(45) Date of Patent: Nov. 3, 2020

(54) MIXED COIL CATHETER AND PROCESS FOR MAKING SAME

(71) Applicant: Inneuroco, Inc., Sunrise, FL (US)

(72) Inventor: Andrew Torres, Sunrise, FL (US)

(73) Assignee: Inneuroco, Inc., Sunrise, FL (US)

( * ) Notice: Subject to any disclaimer, the term of this patent is extended or adjusted under 35 U.S.C. 154(b) by 0 days.

(21) Appl. No.: 16/709,593

(22) Filed: Dec. 10, 2019

(51) Int. Cl.
*A61M 25/00* (2006.01)
*B29D 22/00* (2006.01)
*B29L 31/00* (2006.01)

(52) U.S. Cl.
CPC .... *A61M 25/0053* (2013.01); *A61M 25/0012* (2013.01); *B29D 22/00* (2013.01); *A61M 2025/0059* (2013.01); *B29L 2031/7542* (2013.01)

(58) Field of Classification Search
CPC .......... A61M 25/0053; A61M 25/0012; A61M 2025/0059; B29D 22/00; B29L 2031/7542
See application file for complete search history.

(56) References Cited

U.S. PATENT DOCUMENTS

| | | | |
|---|---|---|---|
| 243,396 | A | 6/1881 | Pfarre |
| 2,211,975 | A | 8/1940 | Hendrickson |
| 2,437,542 | A | 3/1948 | Krippendorf |
| 3,416,531 | A | 12/1968 | Edwards |
| 3,757,768 | A | 11/1973 | Kline |
| 3,924,632 | A | 12/1975 | Cook |
| 4,425,919 | A | 1/1984 | Alston, Jr. et al. |
| 4,430,083 | A | 2/1984 | Ganz et al. |
| 4,484,586 | A | 11/1984 | McMickle et al. |
| 4,516,972 | A | 5/1985 | Samson |
| 4,657,024 | A | 4/1987 | Coneys |
| 4,676,229 | A | 6/1987 | Krasnicki |
| 4,737,153 | A * | 4/1988 | Shimamura ....... A61M 16/0425 604/526 |
| 4,739,768 | A | 4/1988 | Engelson |
| 4,806,182 | A | 2/1989 | Rydell et al. |
| 4,832,681 | A | 5/1989 | Lenck |
| 4,899,787 | A | 2/1990 | Ouchi et al. |
| 4,981,478 | A | 1/1991 | Evard et al. |
| 4,985,022 | A | 1/1991 | Fearnot et al. |
| 5,037,404 | A | 8/1991 | Gold et al. |
| 5,057,092 | A | 10/1991 | Webster, Jr. |
| 5,069,674 | A | 12/1991 | Fearnot et al. |

(Continued)

FOREIGN PATENT DOCUMENTS

| | | |
|---|---|---|
| DE | 3642107 C2 | 6/1987 |
| EP | 0098100 A2 | 1/1984 |

(Continued)

*Primary Examiner* — Amber R Stiles
(74) *Attorney, Agent, or Firm* — Gregory L. Mayback; Dickinson Wright PLLC (57) ABSTRACT

A mixed coil catheter includes a hollow inner liner defining a lumen, having an exterior surface, and defining a middle point, a single support cord coiled around the exterior surface of the inner liner starting from an intermediate point in a distal direction up to a support end plane and then reversed in the proximal direction proximally away from the support end plane at least past the middle point of the inner liner, having a maximum outer diameter, and forming an end wall at the support end plane, and an outer liner covering the inner liner and the support cord to fix the support cord in place.

24 Claims, 3 Drawing Sheets

(56) References Cited

U.S. PATENT DOCUMENTS

| | | |
|---|---|---|
| 5,176,660 A | 1/1993 | Truckai |
| 5,178,158 A | 1/1993 | De Toledo |
| 5,180,376 A | 1/1993 | Fischell |
| 5,184,627 A | 2/1993 | De Toledo |
| 5,217,482 A | 6/1993 | Keith |
| 5,222,949 A | 6/1993 | Kaldany |
| 5,248,305 A | 9/1993 | Zdrahala |
| 5,313,967 A | 5/1994 | Lieber et al. |
| 5,405,338 A | 4/1995 | Kranys |
| 5,951,539 A * | 9/1999 | Nita .................. A61M 25/0053 604/524 |
| 6,575,959 B1 | 6/2003 | Sarge et al. |
| 10,357,638 B2 | 7/2019 | Gulachenski et al. |

FOREIGN PATENT DOCUMENTS

| | | |
|---|---|---|
| EP | 0421650 A1 | 4/1991 |
| FR | 2613231 | 10/1988 |
| JP | H05-220225 | 8/1993 |
| WO | 93/05842 | 4/1993 |
| WO | 93/15785 | 8/1993 |

\* cited by examiner

MIXED COIL CATHETER AND PROCESS FOR MAKING SAME

FIELD OF THE INVENTION

The present systems, apparatuses, and methods lie in the field of catheters. The present disclosure relates to a mixed coil catheter and processes for making the catheter with a minimized outer diameter, in particular, at the junction between a distal end of a catheter-supporting member and a distal tip.

BACKGROUND OF THE INVENTION

Catheters are increasingly used to access remote regions of the human body and, in doing so, delivering diagnostic or therapeutic agents to those sites. In particular, catheters that use the circulatory system as the pathway to these treatment sites are especially practical. Catheters are used to access other regions of the body, e.g., genito-urinary regions, for a variety of therapeutic and diagnostic reasons. One such treatment of diseases of the circulatory system is in the case of thrombotic stroke, in which suction is employed to completely remove an occluding clot from a vessel.

Often the target that one desires to access by catheter is within a soft tissue such as the liver or the brain. These are difficult sites to reach. The catheter must be introduced through a large artery, such as those found in the groin or in the neck, and then be passed through ever-narrower regions of the arterial system until the catheter reaches the selected site. Often such pathways will wind back upon themselves in a multi-looped path. These catheters are difficult to design and to utilize in that they must be fairly stiff at their proximal end to allow the pushing and manipulation of the catheter as it progresses through the body, and yet must be sufficiently flexible at the distal end to allow passage of the catheter tip through the loops and increasingly smaller blood vessels mentioned above and yet, at the same time, not cause significant trauma to the blood vessel or to the surrounding tissue. Further details on the problems and an early, but yet effective, way of designing a catheter for such a traversal may be found in U.S. Pat. No. 4,739,768 to Engel son.

These catheters are designed to be used with a guidewire. A guidewire is a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

The human vasculature is quite complex. It is believed that each person's vasculature is unique and indeed could be used as an identifying characteristic of an individual. Be that as it may, there are a few times when, irrespective of the fine design of a guidewire and enhanced trackability of a specific catheter may not in combination allow access to a specific site in the human body. Multiple turns through a neurological area or decreasing radius arterial turns may require that the catheter be modified for the particular use.

There are other ways of causing a catheter to proceed through the human vasculature to a selected site, but a guidewire-aided catheter is considered to be both quick and more accurate than the other procedures. One such alternative procedure is the use of a flow-directed catheter. These devices often have a small balloon situated on the distal end of the catheter that may be alternately deflated and inflated as the need to select a route for the catheter is encountered.

The use of internal supporting members (e.g., wires, ribbons, braids) in a catheter body is not a novel concept. Typical background patents are discussed below. However, none of these documents have produced a catheter having physical capabilities of the catheter described herein.

There are a number of catheters discussed in the literature that utilize catheter bodies having multiply-wrapped reinforcing material. These catheters include structures having braided bands or ones in which the spirally wound material is simply wound in one direction and the following layer or layers are wound in the same or other directions.

U.S. Pat. No. 2,437,542 to Krippendorf describes a "catheter-type instrument" that is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium that renders the tube stiff yet flexible. The thus-plasticized tubing is then dipped in some other medium to allow the formation of a flexible varnish-like layer. This latter material may be a tung oil base or a phenolic resin and a suitable plasticizer.

Similarly, U.S. Pat. No. 3,416,531 to Edwards, shows a catheter having braiding-edge walls. The device further has additional layers of other polymers such as TEFLON® and the like. The strands found in the braiding in the walls appear to be threads having circular cross-sections. The device is shown to be fairly stiff in that it is designed so that it may be bent using a fairly large handle at its proximal end.

U.S. Pat. No. 3,924,632 to Cook, shows a catheter body utilizing fiberglass bands wrapped spirally for the length of the catheter. As is shown in FIG. 2 and the explanation of the figure at column 3, lines 12 and following, the catheter uses fiberglass bands that are braided, that is to say, bands that are spiraled in one direction cross over and under bands that are spiraled in the opposite direction. Additionally, FIG. 3 depicts a catheter shaft having both an inner lining or core 30 and an outer tube 35.

U.S. Pat. No. 4,425,919 to Alston, Jr. et al., shows a multilayered assembly using multi-stranded flat wire braid. The braid 14 in FIG. 3 further covers an interior tubing or substrate 12.

U.S. Pat. No. 4,484,586 to McMickle et al. shows a method for the production of a hollow, conductive medical tubing. The conductive wires are placed in the walls of hollow tubing specifically for implantation in the human body, particularly, for pacemaker leads. The tubing is preferably made of an annealed copper wire that has been coated with a body-compatible polymer such as a polyurethane or a silicone. After coating, the copper wire is wound into a tube. The wound substrate is then coated with still another polymer to produce a tubing having spiral conducting wires in its wall.

A document showing the use of a helically wound ribbon of flexible material in a catheter is U.S. Pat. No. 4,516,972 to Samson. This device is a guiding catheter and it may be produced from one or more wound ribbons. The preferred ribbon is an aramid material known as "Kevlar 49." This device is fairly stiff and is designed to take a "set" and remain in a particular configuration as another catheter is passed through it. It must be soft enough so as not to cause substantial trauma, but it is not for use with a guidewire.

U.S. Pat. No. 4,806,182 to Rydell et al. shows a device using a stainless steel braid embedded in its wall and having an inner layer of a polyfluorocarbon. The process also described therein is a way to laminate the polyfluorocarbon to a polyurethane inner layer to prevent delamination.

U.S. Pat. No. 4,832,681 to Lenck shows a method and apparatus useful for artificial fertilization. The device itself is a long portion of tubing that, depending upon its specific materials of construction, may be made somewhat stiffer by the addition of a spiral reinforcement comprising stainless steel wire.

U.S. Pat. No. 4,981,478 to Evard et al., discloses a multi-sectioned or composite vascular catheter. The interior section of the catheter has three sections making up the shaft. The most interior (and distal) section, 47, appears to be a pair of coils 13 and 24 having a polymeric tubing member 21 placed therewithin. The next, more proximal, section is 41, and FIG. 4 shows it to be "wrapped or braided" about the next inner layer discussed just above. The drawing does not show it to be braided but, instead, a series of spirally wrapped individual strands. Finally, the outermost tubular section of this catheter core is another fiber layer 49, of similar construction to the middle section 26 discussed just above.

Another catheter showing the use of braided wire is shown in U.S. Pat. No. 5,037,404 to Gold et al. Gold mentions the concept of varying the pitch angle between wound strands to result in a device having differing flexibilities at differing portions of the device. The differing flexibilities are caused by the difference in pitch angle. No mention is made of the use of ribbon, nor is any specific mention made of the particular uses to which the Gold device may be placed.

U.S. Pat. No. 5,057,092 to Webster, Jr., shows a catheter device used to monitor cardiovascular electrical activity or to electrically stimulate the heart. The catheter uses braided helical members having a high modulus of elasticity, e.g., stainless steel. The braid is a fairly complicated, multi-component pattern shown well in FIG. 2.

U.S. Pat. No. 5,176,660 to Truckai shows the production of catheters having reinforcing strands in their sheath wall. The metallic strands are wound throughout the tubular sheath in a helical crossing pattern to produce a substantially stronger sheath. The reinforcing filaments are used to increase the longitudinal stiffness of the catheter for good "pushability." The device appears to be quite strong and is wound at a tension of about 250,000 lb/in$^2$ or more. The flat strands themselves are said to have a width of between 0.006 and 0.020 inches and a thickness of 0.0015 and 0.004 inches.

Another variation that utilizes a catheter wall having helically placed liquid crystal fibrils is found in U.S. Pat. No. 5,248,305 to Zdrahala. The catheter body is extruded through an annular die, having relatively rotating inner and outer mandrel dies. In this way, the tube containing the liquid crystal polymer plastic-containing material exhibits a bit of circumferential orientation due to the rotating die parts. At column 2, line 40 and following, Zdrahala suggests that the rotation rate of the inner and outer walls of the die may be varied as the tube is extruded, with the result that various sections of the extruded tube exhibit differing stiffnesses.

U.S. Pat. No. 5,217,482 to Keith shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

Japanese Kokai 05-220,225, owned by the Terumo Corporation, describes a catheter in which the torsional rigidity of the main body is varied by incorporating onto an inner tubular section 33, a wire layer that is tightly knitted at the proximal section of the catheter and more loosely knitted at a midsection.

There are a variety of catheters that, unlike the devices discussed above, utilize but a single layer of reinforcing material. For instance, U.S. Pat. No. 243,396 to Pfarre, patented in June of 1881, shows the use of a surgical tube having a wire helix situated within the tube wall. The wire helix is said to be vulcanized into the cover of the device.

U.S. Pat. No. 2,211,975 to Hendrickson, shows a similar device also comprising a stainless steel wire 15 embedded in the inner wall of a rubber catheter.

U.S. Pat. No. 3,757,768 to Kline shows a "unitary, combined spring guide-catheter that includes an inner wall portion formed as a continuous helical spring with the helices in contact with each other and an outer wall portion formed from an inert plastic material enclosing the spring in such a manner as to become firmly bonded to the spring while having its outer surface smooth." There is no suggestion to separate the windings of the coil in any fashion.

U.S. Pat. No. 4,430,083 to Ganz describes a catheter used for percutaneous administration of a thrombolytic agent directly to a clot in a coronary artery. The device itself is an elongated, flexible tube supported by helically wound wire having a specific cross-sectional shape. The wire is wound into a series of tight, contiguous coils to allow heat shrinking of tubing onto the outside of the wire of the shape of the outer surface of the wire as wound into the helix provides the heat-shrunk tubing with footing for a tight fit.

U.S. Pat. No. 4,657,024 to Coneys shows a catheter that employs a set of helical strips within the wall of the catheter. However, the helical strips are of a radiopaque material, e.g., fluorinated ethylene-propylene. It is not clear that the blended radiopaque material necessarily provides any physical benefit other than the ability to allow the catheter shaft to be seen when viewed with a fluoroscope.

U.S. Pat. No. 4,737,153 to Shimamura et al. describes a device that is characterized as a "reinforced therapeutic tube" and that uses a spiral reinforcing material embedded within the wall of the device.

U.S. Pat. No. 5,069,674 to Fearnot et al. (and its parent, U.S. Pat. No. 4,985,022) shows a small diameter epidural catheter having a distal tip made up of a stainless steel wire that is helically wound and placed within a tubular sheath or tube. There is no suggestion within Fearnot that the interior coil be made to adhere to the outer tubular sheath.

Similarly, U.S. Pat. No. 5,178,158 to de Toledo shows what is characterized as a "convertible wire for use as a guidewire or catheter." The patent describes a structure comprising an interior wire or spring section shown, in the drawings, to be of generally rectangular cross-section. Outer layers of the device include a polyamide sheath placed adjacent to the helical coil at the proximal end of the catheter (see column 4, lines 64 and following). The device also comprises an outer sheath 40 of Teflon that extends from the proximal end 12 to the distal end 14 of the device. The overlying sheath 40 may extend or overhang at the proximal or the distal end of the catheter. The distal tip portion 13 is said to be "flexible, soft, and floppy."

U.S. Pat. No. 5,184,627 to de Toledo shows a guidewire suitable for infusion of medicaments to various sites along the guidewire. The guidewire is made up of a helically wound coil having a polyamide sheath enclosing its proximal portion and a Teflon sheath tightly covering the entire wire coil. The coil is closed at its distal end. There is no suggestion that the wire forming the helical core be adhesively attached to its outer coverings.

U.S. Pat. No. 5,313,967 to Lieber et al. shows a medical device, a portion of which is a helical coil that apparently may include an outer plastic sheath in some variations. A secondary helix of a somewhat similar design (in that it is formed by rotating a flat wire or the like along its longitudinal axis to form a screw-like configuration) is included within the helical coil to provide axial pushability and torque transmission.

U.S. Pat. No. 5,405,338 to Kranys describes a helically wound catheter incorporating a shaft component having a helically wound coil with a skin or webbing supported by the coil. The skin or webbing is said to contribute "negligibly to the resistance of the catheter to axially directed compressive forces." The catheter may include an inner, taut skin component.

International Patent Application No. WO 00199315785A1 to Sutton et al. describes kink-resistant tubing made up of a thin layer of an encapsulating material and a reinforcing coil. As is shown in the drawings, the supporting material is embedded within the wall of the tubing in each instance.

International Patent Application No. WO 001993005842 to Shin et al. shows a ribbon-wrapped catheter. The device is shown as a section of a dilatation catheter. The inner section 34 is a helically wound coil and is, preferably, a flat wire. See, page 6, lines 25 and following. The coil is then wrapped with a heat-shrunk jacket 34 formed of low-density polyethylene. A lubricious material such as a silicone coating may then be placed on the inner surface of the spring coil to "enhance handling of the guidewire". It is also said, on page 6 of the document, that the "entire spring coil, before it is wound or jacketed, may be coated with other materials such as Teflon® to enhance lubricity or provide other advantages. In some embodiments, the spring coil has been plated with gold."

U.S. Pat. No. 5,951,539 to Nita et al. describes a catheter with a single coil at a distal portion and a cross-coil at a proximal portion. This particular configuration is taught because it is understood that less support at the distal end leads to better flexibility, thus cross-coil is tolerated in the proximal and intermediate sections of the catheter but, where the most flexibility is desired—at the distal end, that portion must be of a single coil structure.

Various endoscopic structures, used primarily in sizes that are larger than endovascular catheters utilize structures including stiffener materials.

U.S. Pat. No. 4,676,229, to Krasnicki et al. describes an endoscopic structure 30 having an ultra-thin walled tubular substrate 31 formed of a lubricious material such as TEFLON®. The structure contains a filament-supported substrate. The filament is coated with and embedded into a filler material, typically an elastomeric material. A highly lubricious outer coating 35, all as shown in FIG. 2, forms the outer layer of the device. FIG. 3 in Krasnicki describes another variation of the endoscopic device in which a different selection of polymer tubing is utilized but the placement of the filamentary support remains varied in an intermediate material of an elastomer. In some variations of the device, see column 3, lines 50 and following, the filament is strongly bonded to the inner tubular substrate using an adhesive 37 "such as an epoxy cement having sufficient bond strength to hold the filament to the substrate as it is deformed into a tight radius."

U.S. Pat. No. 4,899,787, to Ouchi et al. (and its foreign relative, German Offenlegungsshrifft DE-3242449) describes a flexible tube for use in an endoscope having a flexible, basic tubular core structure made up of three parts. The three parts are an outer meshwork tube, an intermediate thermoplastic resin tube bonded to the outer meshwork tube, and an inner ribbon made of a stainless steel or the like that is adherent to the two polymeric and meshwork tubes such that the resin tube maintains an adherent compressive pressure in the finished flexible tube. Ouchi also suggests, at column 2, lines 48 and following, the production of an endoscope tube having "flexibility which varies in step-wise manner from one end of the tube to the other . . . and is produced by integrally bonding two or more thermoplastic resin tube sections formed of respective resin materials having different hardnesses to the outer surface of the tubular core structure . . . ."

U.S. Pat. No. 5,180,376 to Fischell describes an introducer sheath utilizing a thin, flat wire metal coil surrounded only on its exterior surface with a plastic tube of coating. The flat wire coil is placed there to lower the "resistance of the sheath to buckling while minimizing the wall thickness of the sheath." A variation using two counter-wound metal ribbons is also described. No suggestion of the use of an adhesive is made in Fischell.

European Patent Application EP0098100A2 to Takagi describes a flexible tube for an endoscope that uses a helically wound metallic strip having a braided covering contiguous to the outer surface of the coil and having still further out a polymeric coating 9. Interior to the coil is a pair of slender flexible sheaths that are secured to a "front-end piece 10" by soldering.

French Patent Document 2,613,231 to Huguenin describes a medical probe used with an endoscope or for some other device used to stimulate the heart. The device appears to be a helix having a spacing between 0 and 0.25 mm (see page 4, line 20) preferably rectangular in cross section (see Page 4, Line 1) and of a multi-phase alloy such as MP35N®, SYNTACOBEN®, or ELGILOY® (see page 4).

German Offenlegungsshrifft DE-3642107 to Morishita describes an endoscope tube, formed of a spiral tube, a braid formed of fibers interwoven into a net (which braid is fitted on the outer peripheral surface of the spiral tube), and a sheath covering the outer peripheral surface of the braid.

U.S. Pat. No. 5,222,949, to Kaldany describes a tube in which a number of circumferential bands are placed at regular intervals along a catheter shaft. The bands may be integrated into the wall of the catheter. A variety of methods for producing the bands in the tubular wall are discussed. These methods include periodically irradiating the wall to produce bands of a higher integral of cross-linking.

European Patent Application No. EP0421650A1 to Frassica describes a method for producing a catheter from a roll of polymer film while incorporating other materials such as tinfoil elements or the like.

Thus, a need exists to overcome the problems with the prior art systems, designs, and processes as discussed above.

SUMMARY OF THE INVENTION

The systems, apparatuses, and methods described provide a flexible catheter that overcome the hereinafore-mentioned disadvantages of the heretofore-known devices and methods of this general type and that provide such features with a decreased outer diameter, in particular, at the junction between the distal tip and the distal end of the catheter-supporting member.

The devices and processes are adaptable and may be used in a variety of catheter formats. The construction technique has the benefit of producing a neurological catheter having the smallest maximum outer diameter but with exceptional strength, resistance to kinking, and recovery from kinking (even in vivo) should such kinking occur. The devices may be used in conjunction with a guidewire.

As used herein, the term "pitch" is defined as a distance between the two sides of an individual coil. As used herein, the term "single coil" is defined as a coiling pattern in which a single wire is dispensed along a longitudinal length at a predetermined pitch. The pitch can be varied along the length. As used herein, the term "cross-coil" is defined as a coiling pattern in which there is a bottom layer and a top layer of a coil angled in opposite directions of each other. The pitch for the bottom and top layers can be the same or they can differ from each other and vary along the length.

With the foregoing and other objects in view, there is provided, a mixed coil catheter comprising a hollow inner liner defining a lumen, having an exterior surface, and defining a middle point, a single support cord coiled around the exterior surface of the inner liner starting from an intermediate point in a distal direction up to a support end plane and then reversed in the proximal direction proximally away from the support end plane at least past the middle point of the inner liner, having a maximum outer diameter, and forming an end wall at the support end plane, and an outer liner covering the inner liner and the support cord to fix the support cord in place.

With the objects in view, there is also provided a mixed coil catheter comprising a hollow inner liner defining a lumen and having an exterior surface, a single support cord coiled around the exterior surface of the inner liner starting from an intermediate point in a distal direction up to a support end plane and then reversed in the proximal direction proximally away from the support end plane, having a maximum outer diameter, and forming an end wall at the support end plane, a distal marker band having a proximal side and a band outer diameter, the marker band disposed about the inner liner to place the proximal side adjacent the end wall, and an outer liner covering the inner liner, the support cord and the marker band to fix the support cord and the marker band in place such that the band outer diameter is no greater than the maximum outer diameter of the support cord.

With the objects in view, there is also provided a method for manufacturing the mixed coil catheter with the steps of placing an inner liner onto a mandrel, the inner liner defining a proximal end, a distal end, and a middle point, loading the mandrel with the inner liner into a coil winder having a proximal connector adjacent the proximal end, applying tension to the mandrel, temporarily securing a first end of a single support cord one of adjacent the proximal connector and to the proximal connector, spinning the mandrel in a first direction to wind the support cord about the inner liner over a first portion at a first pitch, at an intermediate point, continuing to wind the support cord about the inner liner over a second portion at a second pitch to create a pitch transition, reversing the mandrel in a second direction opposite the first direction and continuing to wind the support cord at the second pitch, the support cord forming an end wall along a support end plane orthogonal to an axis of the mandrel, the end wall facing the distal end of the inner liner and having a given outer diameter, continuing to rotate the mandrel in the second direction until the support cord is adjacent the pitch transition and creates a last-crossed position, while keeping tension on the support cord, the securement of the first end is removed to loosen a proximal length of the support cord from the first end to the last-crossed position as a loose wire, trimming the loose wire from the inner liner adjacent the last-crossed position, continuing to rotate the mandrel in the second direction to wind the support cord at a third pitch in the proximal direction past the last-crossed position to an endpoint that is proximal of the middle point of the inner liner, cutting the support cord at the endpoint to create a second end and securing the second end to the inner liner at the endpoint, sliding a marker band having an outer diameter equal to or less than the given outer diameter over the distal end of the inner liner to place a proximal side of the marker band against the end wall, sealing an exterior of the inner liner, the support cord, and the marker band with a coating as an outer liner to fix the support cord and the marker band in place such that the outer diameter of the marker band is no greater than the maximum outer diameter of the support cord wrapped around the inner liner, and removing the inner liner, the support cord, the marker band, and the outer liner from the mandrel to form a mixed coil catheter.

In accordance with another feature, there is provided a distal marker band having a proximal side and a band outer diameter, the marker band disposed about the inner liner to place the proximal side adjacent the end wall, the outer liner covering the marker band to fix the support cord and the marker band in place such that the band outer diameter is no greater than the maximum outer diameter of the support cord.

In accordance with a further feature, the inner liner is an extrusion of at least one of ethylene chlorotrifluoroethylene, EFEP, ethylene tetrafluoroethylene, fluorinated ethylene propylene, liquid crystal polymer, nylon, polyethylene, polyether ether ketone, polyethylene terephthalate, perfluoroalkoxy, polytetrafluoroethylene, polyvinylidene fluoride, and tetrafluoroethylene hexafluoropropylene vinylidene fluoride.

In accordance with an added feature, the inner liner has a wall thickness of between approximately 0.0127 mm and approximately 2.54 mm.

In accordance with an additional feature, the inner liner is approximately 0.00075" thick.

In accordance with yet another feature, the support cord is a flat stainless steel wire having a cross-sectional dimension of approximately 0.51 mm by approximately 0.2 mm.

In accordance with yet a further feature, the support cord is a flat wire having a thickness in the range of between approximately 0.0051 mm to 25.4 mm and a width in the range of between approximately 0.0508 mm to 25.4 mm.

In accordance with yet an added feature, the support cord is a round wire having a thickness in the range of between approximately 0.0127 mm to 12.7 mm.

In accordance with yet an additional feature, the support cord is of a material of at least one of a stainless steel alloy, a titanium alloy, a nickel alloy, a cobalt alloy, a nitinol alloy, a copper clad aluminum, a stainless clad copper, and tungsten.

In accordance with again another feature, the securing of the first end is performed with an adhesive.

In accordance with again a further feature, the first pitch is in the range of between approximately 0.0127 mm to 25.4 mm.

In accordance with again an added feature, the second pitch is approximately 0.66 mm.

In accordance with again an additional feature, the reversing step is carried out by wrapping the support cord completely around the inner liner along the support end plane to form the end wall.

In accordance with still another feature, the third pitch is the same as the second pitch.

In accordance with a concomitant feature, the third pitch is different from the second pitch.

Although the systems, apparatuses, and methods are illustrated and described herein as embodied in a mixed coil catheter and processes for making the catheter with a minimized outer diameter, it is, nevertheless, not intended to be limited to the details shown because various modifications and structural changes may be made therein without departing from the spirit of the invention and within the scope and range of equivalents of the claims. Additionally, well-known elements of exemplary embodiments will not be described in detail or will be omitted so as not to obscure the relevant details of the systems, apparatuses, and methods.

Additional advantages and other features characteristic of the systems, apparatuses, and methods will be set forth in the detailed description that follows and may be apparent from the detailed description or may be learned by practice of exemplary embodiments. Still other advantages of the systems, apparatuses, and methods may be realized by any of the instrumentalities, methods, or combinations particularly pointed out in the claims.

Other features that are considered as characteristic for the systems, apparatuses, and methods are set forth in the appended claims. As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one of ordinary skill in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the systems, apparatuses, and methods of the invention that are regarded as novel, it is believed that the systems, apparatuses, and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the systems, apparatuses, and methods. Advantages of embodiments of the systems, apparatuses, and methods will be apparent from the following detailed description of the exemplary embodiments thereof, which description should be considered in conjunction with the accompanying drawings in which.

DETAILED DESCRIPTION OF THE EMBODIMENTS

As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one skilled in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the features of the systems, apparatuses, and methods that are regarded as novel, it is believed that the systems, apparatuses, and methods will be better understood from a consideration of the following description in conjunction with the drawing figures, in which like reference numerals are carried forward.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Alternate embodiments may be devised without departing from the spirit or the scope of the invention. Additionally, well-known elements of exemplary embodiments of the systems, apparatuses, and methods will not be described in detail or will be omitted so as not to obscure the relevant details of the systems, apparatuses, and methods.

Before the systems, apparatuses, and methods are disclosed and described, it is to be understood that the terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact (e.g., directly coupled). However, "coupled" may also mean that two or more elements are not in direct contact with each other, but yet still cooperate or interact with each other (e.g., indirectly coupled).

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, top/bottom, and proximal/distal. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

Herein various embodiments of the systems, apparatuses, and methods are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments. Referring now to the figures of the drawings in detail and first, particularly to FIGS. 1 to 8, there is shown a first exemplary embodiment of a mixed coil catheter 100 and processes for constructing the catheter 100 with a minimized outer diameter on a catheter manufacturing machine 1. The machine 1 has opposing chuck parts 20, 22 and a mandrel 10 and is not shown in further detail. An exemplary embodiment of the machine 1 is a Roth Greaves Automatic Coil Winder, and an example of the mandrel 10 is a silver coated copper (SCC) column having a diameter of approximately 2.34 mm/0.092".

The exemplary embodiment of the catheter 100 is made on the mandrel 10, which is held on either side by a respective one of the chucks 20, 22. In an exemplary configuration, the mandrel 10 has a diameter of between approximately 0.254 mm/0.010" to approximately 12.7 mm/0.500". Exemplary materials for the mandrel 10 include stainless steel alloys, titanium alloys, nickel alloys, cobalt alloys, nitinol alloys, copper clad aluminum, stainless clad copper, tungsten, silver, and/or copper, to name a few.

Figure 1:
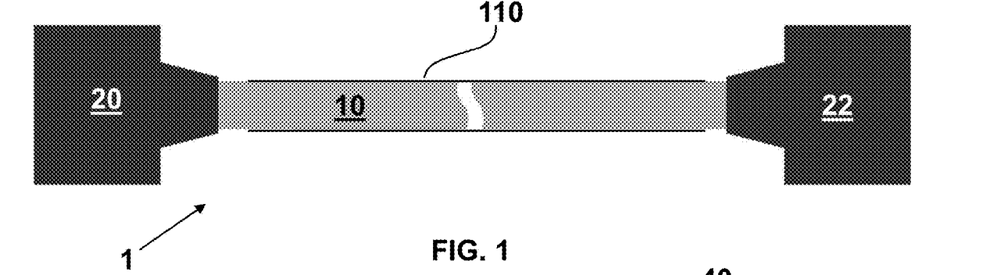
FIG. 1 is a fragmentary, longitudinally cross-sectional view of portions of a catheter manufacturing machine and an inner layer of a catheter to be manufactured by the machine.

To start an exemplary process of creating the catheter 100, as shown in FIG. 1, an inner layer or liner or core 110 is loaded onto the mandrel 10. An exemplary embodiment of the inner liner 110 is an approximately 0.00075" thick extrusion of etched Polytetrafluoroethylene (PTFE). Alternative embodiments for the extrusion include a wall thickness of between approximately 0.0127 mm/0.0005" and approximately 2.54 mm/0.1000". Exemplary materials for the inner liner include ethylene chlorotrifluoroethylene (ECTFE), EFEP, ethylene tetrafluoroethylene (ETFE), fluorinated ethylene propylene (FEP), liquid crystal polymer (LCP), nylon, polyethylene (PE), polyether ether ketone (PEEK), polyethylene terephthalate (PET/PETE), perfluoroalkoxy (PFA), polytetrafluoroethylene (PTFE), polyvinylidene fluoride (PVDF), and/or tetrafluoroethylene hexafluoropropylene vinylidene fluoride (THV).

The mandrel 10 with the inner liner 110 is loaded into the coil winder by securing the mandrel 10 into the machine's right and left chucks 20, 22. Tension is applied to the mandrel 10 to reduce vibration during a winding process. When the mandrel 10 is mounted on the chucks 20, 22, the winding machine causes the chucks 20, 22 to spin, thereby allowing dispensation of a coiled support structure about and along a length of the mandrel 10.

Figure 2:
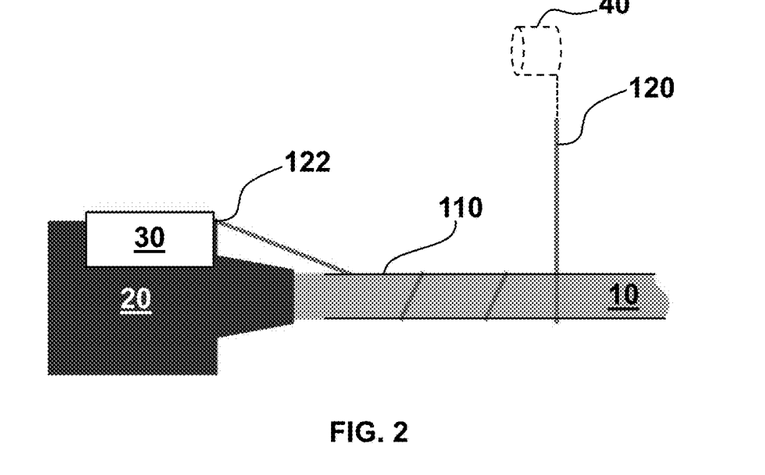
FIG. 2 is a fragmentary, side elevational view of a proximal end of the machine of FIG. 1 with a support cord temporarily secured at a first end to a proximal chuck and beginning to be wrapped at a first pitch around the inner liner disposed on a mandrel with the opposite end of the support cord being unwound from a spool, shown in dashed lines.
Figure 3:
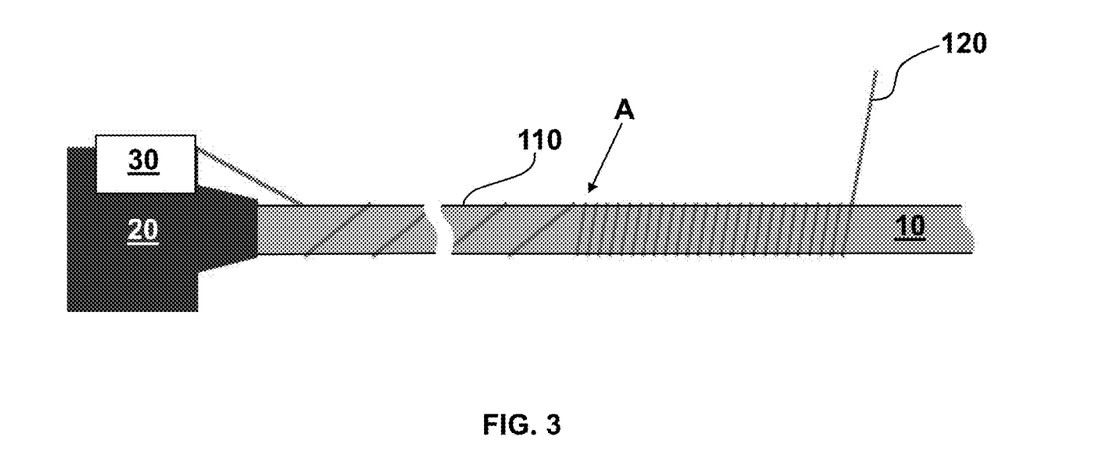
FIG. 3 is a fragmentary, side elevational view of a distal portion of the machine of FIG. 1 with the support cord further wrapped at a second pitch around the inner liner.

A support cord 120 is to be wound on the inner liner 110. In this exemplary embodiment, a first end 122 of the support cord 120 is temporarily secured to a proximal chuck 20. This securement 30 can be effected by an adhesive, such as painter's tape, as shown in FIG. 2. Herein, the word "cord" is used with respect to, for example, the support cord 120. This word is meant to be broad and not limited to a particular material or cross-section. The term cord refers to any longitudinally extending material that can comprise the structure and function described herein. As defined herein, the term cord is not limited to a single cord; a cord can be a plurality of cords as well. Therefore, cord and cords are used interchangeably. Cords also are not limited to a particular type of material. The material can be made of natural fibers, man-made or synthetic fibers, plastics, and/or metals, to name a few. Cords also are not limited to a particular structure. The material can be made of twisted strands, twisted strands with a central core, or a single strand or wire, to name a few. The shape of the wire can be flat and/or round. One exemplary embodiment described herein is a flat stainless steel (SS) wire having a cross-sectional dimension of approximately 0.51 mm/0.0020" by approximately 0.2 mm/0.0080". The embodiments described herein, however, are not limited to SS wire, even though the example of SS wire is referred to or is used herein. An exemplary embodiment for the thickness of a flat wire variation is in the range of between approximately 0.0051 mm/0.0002" to 25.4 mm/0.1000". An exemplary embodiment for the width of a flat wire variation is in the range of between approximately 0.0508 mm/0.002" to 25.4 mm/1.0". An exemplary embodiment for the thickness of a round wire variation is in the range of between approximately 0.0127 mm/0.0005" to 12.7 mm/0.500". Exemplary embodiments of materials for the cord include stainless steel alloys, titanium alloys, nickel alloys, cobalt alloys, nitinol alloys, copper clad aluminum, stainless clad copper, and tungsten.

Figure 4:
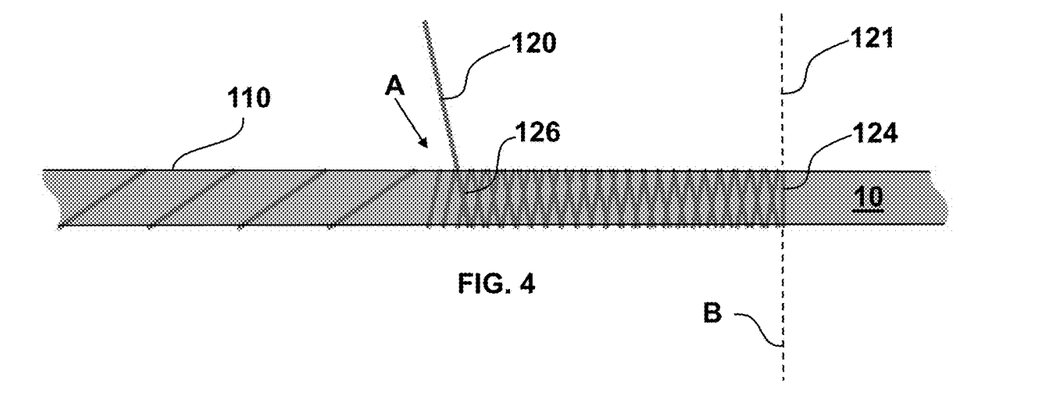
FIG. 4 is a fragmentary, side elevational view of a distal intermediate portion of the machine of FIG. 1 with the support cord further wrapped at a second pitch around the inner liner.

The support cord 120 is dispensed from a spool 40 and is wrapped around the mandrel 10 a few times, as shown in FIG. 2. The chucks 20, 22 are rotated and the support cord 120 is dispensed from the spool 40 along a length of the inner liner 110. In an exemplary embodiment, the support cord 120 is dispensed at a wide pitch of approximately 25.4 mm/1.0" across the mandrel for approximately 1 m/39.20". At that point ("A" in FIG. 3), the pitch is tightened to an approximately 0.66 mm/0.026" pitch for approximately 18 cm/7.09". As shown in FIG. 4, the dispensing direction is reversed and the support cord 120 continues to be dispensed at the same 0.026" pitch. At the reversing position, before the pitch is completely reversed, the support cord 120 is wrapped partially or fully around the mandrel 10 along a support end plane 121 orthogonal to the axis of the mandrel 10. Therefore, an end wall 124 is formed by the support cord 120 along the support end plane 121 extending radially outward from the outer surface of the inner liner 110, the end wall 124 facing the distal end of the catheter 100. This reversed wrap of the support cord 120 is stopped just short of the pitch transition A by ceasing rotation of the mandrel 10. The point on the mandrel 10 where the reversed portion of the support cord 120 touches and crosses a proximal-most coil of the forward portion is referred to herein as a last-crossed position 126.

An exemplary embodiment for the pitch of a single coil is in the range of between approximately 0.0127 mm/0.0005" to 25.4 mm/1.00". An exemplary embodiment for the pitch of a bottom/inner coil in a cross-coil winding is in the range of between approximately 0.0127 mm/0.0005" to 25.4 mm/1.00" and an exemplary embodiment for the pitch of a top/outer coil in the cross-coil winding is in the range of between approximately 0.0127 mm/0.0005" to 25.4 mm/1.00".

Figure 5:
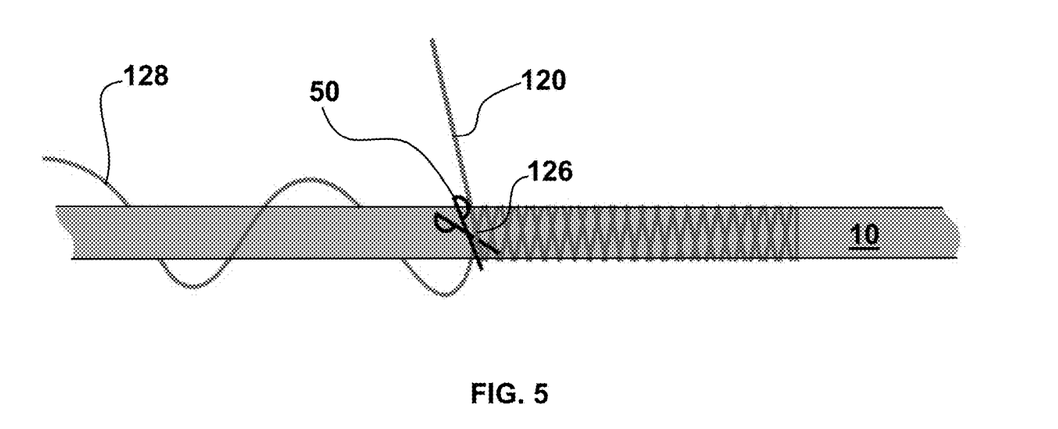
FIG. 5 is a fragmentary, side elevational view of the distal intermediate portion of the machine of FIG. 4 with the distal end of the support cord held at a last-crossed position and with a proximal end of the support cord loosened and being trimmed off from the inner liner.
Figure 6:
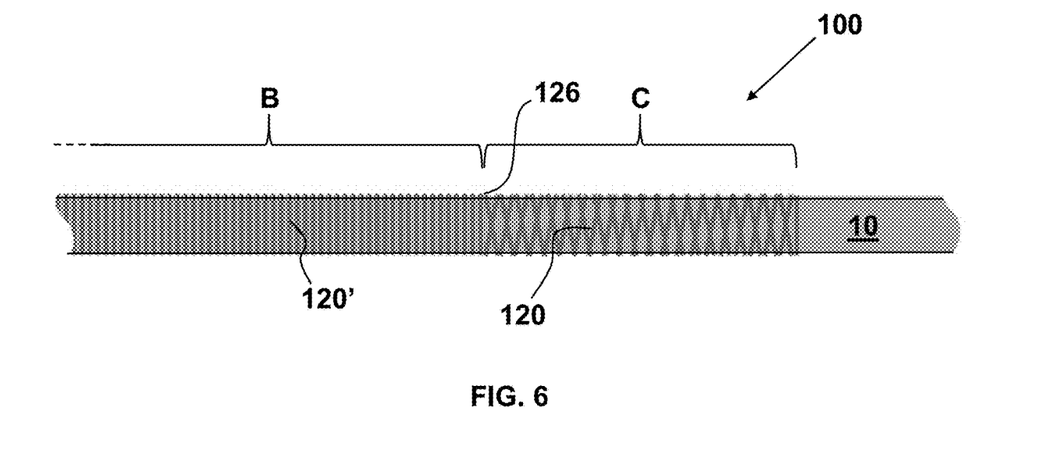
FIG. 6 is a fragmentary, side elevational view of the distal intermediate portion of the machine of FIG. 5 with the distal end of the support cord further wrapped in the proximal direction at a second pitch around the inner liner starting from the last-crossed position.
Figure 7:
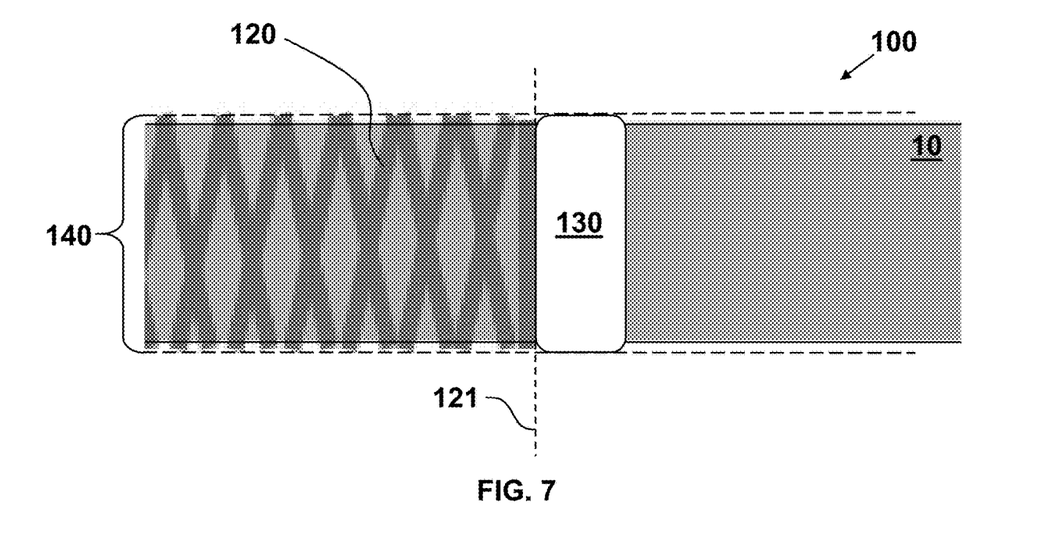
FIG. 7 is a fragmentary, enlarged, side elevational view of an intermediate portion of an exemplary embodiment of a multi-coil catheter with a marker band adjacent an end wall of the support cord.
Figure 8:
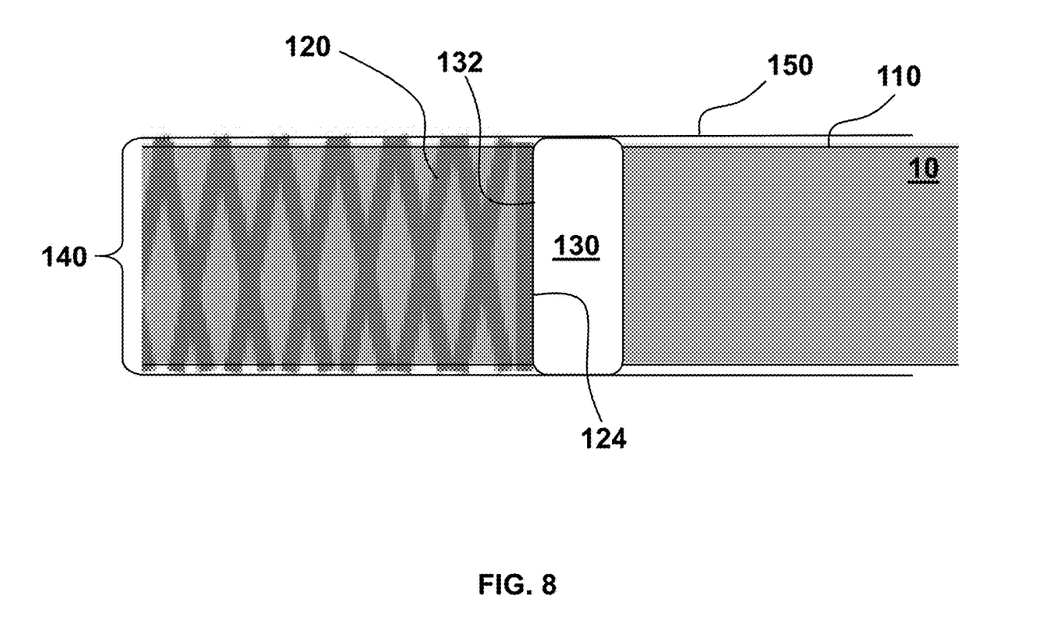
FIG. 8 is a fragmentary, enlarged, side elevational view of the intermediate portion of the multi-coil catheter of FIG. 7 with an outer liner covering the support cord and the marker band.

With tension kept on the support cord 120, the securement 30 on the chuck 20 retaining the first end 122 is removed, thereby loosening the entire proximal length of the support cord 120 up to the last-crossed position 126, this portion of the support cord 120 is referred to as a loose wire 128. As shown in FIG. 5, the loose wire 128 is trimmed (e.g., with a fine-wire trimmer) as close as possible to the last-crossed position 126. The loose wire 128 is removed from the mandrel 10 (and discarded). The support cord 120 can remain at the same pitch or it can be changed to a different pitch before further rotation of the mandrel 10 commences. In the exemplary configuration of FIG. 6, the support cord 120' is angled to a different pitch (e.g., 0.012") in a segment B proximal of the last-crossed position 126 and rotation of the mandrel 10 restarts and continues winding of the support cord 120' in the proximal direction to a desired length on the catheter 100.

The catheter 100 having the above features and manufactured as described has various significant features. One beneficial advantage is that, only with a single wire winding, both a distal cross-coil portion C and a single proximal wire portion B can create the catheter 100. With prior art catheters where a single wire was used and terminated at the distal end, something was required to hold the distal end of the support wire down. This holding device could be a marker band, for example. The holding device could be an adhesive but a marker band would still be necessary at that termination point. In either configuration, the outer diameter would, by necessity, have to increase beyond the outer diameter of the support coil/wire/braid because the adhesive and/or the marker band is located on the outer circumferential surface of the support coil. A further disadvantage to this is that the overlap decreases flexibility of the catheter at the segment where the overlap is present. A third disadvantage of having a terminating end of the support coil is that there is a distinct possibility that the end springs up off of the outer surface of the catheter, for example, when subjected to the extreme bending that such catheters undergo when traversing tortuous anatomy.

In contrast, the catheter 100 provides a distal end with no requirement for enlarging the outer diameter. This advantageous property is illustrated with regard to FIG. 7, which shows an enlarged distal portion of the catheter 100 of FIG. 6. Here, the dashed lines show a maximum outer diameter 140 to which the support cord 120 projects radially outwards from the outer surface of the inner liner 110. Any adhesive or marker band that would be used to hold down the support cord 120 from this outer surface, by definition, would increase the maximum outer diameter 140 of the catheter 100, at least at this junction. By forming the support cord 120 with the end wall 124, however, the structure of the end wall 124 forms an end stop used to minimize the maximum outer diameter 140. In particular, a marker band 130 is provided at the distal portion of the catheter 100, the marker band 130 having an inner diameter equal to or greater than the outer diameter of the inner liner 110 and an outer diameter no greater than the maximum outer diameter 140. After the mandrel 10 is separated from the distal chuck 22, this marker band 130 is slid over the inner liner 110 until a proximal side 132 of the marker band 130 is adjacent to or abuts the end wall 124. If desired, the mandrel 10 is reconnected to the distal chuck 22. The catheter 100 is completed by disposing an outer liner/outer layer 140 directly on top of the support cord 120 and the marker band 130. Accordingly, the maximum outer diameter 140 is preserved even though a marker band 130 is present at the distal end of the support cord 120. This configuration minimizes the maximum outer diameter 140 at the distal end to provide the thinnest possible wall of the catheter 100 with which to navigate into the smallest possible vessel. Further, by fixing the marker band 130 at the end wall 124 along the support end plane 121, the distal end of the support cord 120 is captured and held without any need for an adhesive. This is a significant benefit because any adhesive at that area would increase the maximum outer diameter 140 of the catheter 100. In other words, there are no ancillary structures or products that are required to capture and hold the end wall 124 at the distal end where it is placed during manufacture.

Current neurological catheters access the brain vessels through a femoral vessel access. This is a long and tortuous path. Further, access through the femur causes a trauma at the entry site. It would be desirable to have an alternative access point for a neurological catheter that is closer to the brain's target vessels and at a site that heals quickly and suffers less trauma when accessed. One desirable site is through a radial access at the wrist. However, prior art catheters are too large for this access (>6 Fr) and, therefore, attempts at using such prior art catheters causes undesirable trauma. The only way to accomplish radial access is with the smallest possible catheter, which is achieved with the instant embodiments. A neurological catheter with the instant embodiments can access, e.g., the Circle of Willis, through a radial vessel as the maximum outer diameter 140 can be 6 Fr or less.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the systems, apparatuses, and methods. However, the systems, apparatuses, and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems, apparatuses, and methods as defined by the following claims.

What is claimed is:

1. A mixed coil catheter, comprising:
    a hollow inner liner defining a lumen and having an exterior surface;
    a single support cord:
        coiled around the exterior surface of the inner liner starting from an intermediate point of the inner liner in a distal direction up to a support end plane and then reversed in a proximal direction proximally away from the support end plane at least past the intermediate point of the inner liner, the support cord being in direct contact with the exterior surface of the inner liner at the intermediate point;
        having a maximum outer diameter, and
        forming an end wall at the support end plane; and
    an outer liner covering the inner liner and the support cord to fix the support cord in place.

2. The catheter according to claim 1, which further comprises a distal marker band having a proximal side and a band outer diameter, the marker band disposed about the inner liner to place the proximal side adjacent the end wall, the outer liner covering the marker band to fix the support cord and the marker band in place such that the band outer diameter is no greater than the maximum outer diameter of the support cord.

3. The catheter according to claim 1, wherein the inner liner is an extrusion of at least one of ethylene chlorotrifluoroethylene, EFEP, ethylene tetrafluoroethylene, fluorinated ethylene propylene, liquid crystal polymer, nylon, polyethylene, polyether ether ketone, polyethylene terephthalate, perfluoroalkoxy, polytetrafluoroethylene, polyvinylidene fluoride, and tetrafluoroethylene hexafluoropropylene vinylidene fluoride.

4. The catheter according to claim 3, wherein the inner liner has a wall thickness of between approximately 0.0127 mm and approximately 2.54 mm.

5. The catheter according to claim 3, wherein the inner liner is approximately 0.00075" thick.

6. The catheter according to claim 1, wherein the support cord is a flat stainless steel wire having a cross-sectional dimension of approximately 0.51 mm by approximately 0.2 mm.

7. The catheter according to claim 1, wherein the support cord is a flat wire having a thickness in a range of between approximately 0.0051 mm to 25.4 mm and a width in a range of between approximately 0.0508 mm to 25.4 mm.

8. The catheter according to claim 1, wherein the support cord is a round wire having a thickness in a range of between approximately 0.0127 mm to 12.7 mm.

9. The catheter according to claim 1, wherein the support cord is made of a material of at least one of a stainless steel alloy, a titanium alloy, a nickel alloy, a cobalt alloy, a nitinol alloy, a copper clad aluminum, a stainless clad copper, and tungsten.

10. A method for manufacturing the mixed coil catheter of claim 1, which comprises:
    placing the inner liner onto a mandrel, the inner liner defining a proximal end, a distal end, and a middle point;

loading the mandrel with the inner liner into a coil winder having a proximal connector adjacent the proximal end;

applying tension to the mandrel;

temporarily securing a first end of the single support cord one of:
 adjacent the proximal connector; and
 to the proximal connector;

spinning the mandrel in a first direction to wind the support cord about the inner liner over a first portion at a first pitch;

at an intermediate point, continuing to wind the support cord about the inner liner over a second portion at a second pitch to create a pitch transition;

reversing the mandrel in a second direction opposite the first direction and continuing to wind the support cord at the second pitch the support cord forming the end wall along the support end plane orthogonal to an axis of the mandrel, the end wall facing the distal end of the inner liner and having a given outer diameter;

continuing to rotate the mandrel in the second direction until the support cord is adjacent the pitch transition and creates a last-crossed position:

while keeping tension on the support cord, the securement of the first end is removed to loosen a proximal length of the support cord from the first end to the last-crossed position as a loose wire:

trimming the loose wire from the inner liner adjacent the last-crossed position;

continuing to rotate the mandrel in the second direction to wind the support cord at a third pitch in the proximal direction past the last-crossed position to an endpoint that is proximal of the middle point of the inner liner;

cutting the support cord at the endpoint to create a second end and securing the second end to the inner liner at the endpoint;

sliding a marker band having an outer diameter equal to or less than the given outer diameter over the distal end of the inner liner to place a proximal side of the marker band against the end wall;

sealing an exterior of the inner liner, the support cord, and the marker band with a coating as the outer liner to fix the support cord and the marker band tin place such that the outer diameter of the marker band is no greater than the maximum outer diameter of the support cord wrapped around the inner liner; and removing the inner liner, the support cord, the marker band, and the outer liner from the mandrel to form a mixed coil catheter.

11. The method according to claim 10, wherein the securing of the first end is performed with an adhesive.

12. The method according to claim 10, wherein the first pitch is in a range of between approximately 0.0127 mm to 25.4 mm.

13. The method according to claim 10, wherein the second pitch is approximately 0.66 mm.

14. The method according to claim 10, wherein the reversing step is carried out by wrapping the support cord completely around the inner liner along the support end plane to form the end wall.

15. The method according to claim 10, wherein the third pitch is the same as the second pitch.

16. The method according to claim 10, wherein the third pitch is different from the second pitch.

17. A mixed coil catheter, comprising:
 a hollow inner liner defining a lumen and having an exterior surface;
 a single support cord:
  coiled around the exterior surface of the inner liner starting from an intermediate point in a distal direction up to a support end plane and then reversed in a proximal direction proximally away from the support end plane at least past the intermediate point, the support cord being in direct contact with the exterior surface of the inner liner at the intermediate point;
  having a maximum outer diameter; and
  forming an end wall at the support end plane;
 a distal marker band having a proximal side and a band outer diameter, the marker band disposed about the inner liner to place the proximal side adjacent the end wall; and
 an outer liner covering the inner liner, the support cord and the marker band to fix the support cord and the marker band in place such that the band outer diameter is no greater than the maximum outer diameter of the support cord.

18. The catheter according to claim 17, wherein the inner liner is an extrusion of at least one of ethylene chlorotrifluoroethylene, EFEP, ethylene tetrafluoroethylene, fluorinated ethylene propylene, liquid crystal polymer, nylon, polyethylene, polyether ether ketone, polyethylene terephthalate, perfluoroalkoxy, polytetrafluoroethylene, polyvinylidene fluoride, and tetrafluoroethylene hexafluoropropylene vinylidene fluoride.

19. The catheter according to claim 18, wherein the inner liner has a wall thickness of between approximately 0.0127 mm and approximately 2.54 mm.

20. The catheter according to claim 18, wherein the inner liner is approximately 0.00075" thick.

21. The catheter according to claim 17, wherein the support cord is a flat stainless steel wire having a cross-sectional dimension of approximately 0.51 mm by approximately 0.2 mm.

22. The catheter according to claim 17, wherein the support cord is a flat wire having a thickness in a range of between approximately 0.0051 mm to 25.4 mm and a width in a range of between approximately 0.0508 mm to 25.4 mm.

23. The catheter according to claim 17, wherein the support cord is a round wire having a thickness in a range of between approximately 0.0127 mm to 12.7 mm.

24. The catheter according to claim 17, wherein the support cord is made of a material of at least one of a stainless steel alloy, a titanium alloy, a nickel alloy, a cobalt alloy, a nitinol alloy, a copper clad aluminum, a stainless clad copper, and tungsten.

* * * * *